(12) United States Patent
Wang et al.

(10) Patent No.: US 12,576,184 B1
(45) Date of Patent: Mar. 17, 2026

(54) CORALLINE HYDROXYAPATITE AND PREPARATION METHOD THEREOF

(71) Applicant: WitKang Zhiyuan Medical Devices (Xi'an) Co., Ltd., Xi'an City (CN)

(72) Inventors: Jiuna Wang, Xi'an City (CN); Liang Chen, Xi'an City (CN); Ya Wang, Xi'an City (CN); Yanting Li, Xi'an City (CN); Jianing Hou, Xi'an City (CN); Yuan Li, Xi'an City (CN)

(73) Assignee: WitKang Zhiyuan Medical Devices (Xi'an) Co., Ltd., Xi'an City (CN)

( * ) Notice: Subject to any disclaimer, the term of this patent is extended or adjusted under 35 U.S.C. 154(b) by 0 days.

(21) Appl. No.: 19/247,635

(22) Filed: Jun. 24, 2025

(30) Foreign Application Priority Data

Jan. 10, 2025 (CN) .......................... 202510045735.4

(51) Int. Cl.
  *A61L 27/12* (2006.01)
  *A61L 27/56* (2006.01)
(52) U.S. Cl.
  CPC ............... *A61L 27/12* (2013.01); *A61L 27/56* (2013.01); *A61L 2430/02* (2013.01)
(58) Field of Classification Search
  None
  See application file for complete search history.

(56) References Cited

U.S. PATENT DOCUMENTS 4,976,736 A 12/1990 White et al.
7,507,257 B2 * 3/2009 Cole ....................... C04B 28/14
623/23.62

(Continued)

FOREIGN PATENT DOCUMENTS

CN 1161305 A 10/1997
CN 1203189 A 12/1998
(Continued)

OTHER PUBLICATIONS

Machine translation of CN 1404880 A, Mar. 26, 2003. (Year: 2003).*

(Continued)

*Primary Examiner* — Sue X Liu
*Assistant Examiner* — Casey S Hagopian
(74) *Attorney, Agent, or Firm* — Hamilton, Brook, Smith & Reynolds, P.C.

(57) ABSTRACT

A coralline hydroxyapatite having a pore size of 30 μm to 1300 μm, a porosity of 50% to 70%, and a conversion rate of 50% or more, and a preparation method are disclosed. The preparation method comprises: soaking pretreated corallite in a cutting protective agent, and then cutting to obtain cut corallite, and screening for cut corallite that meets a cutting size requirement to obtain an acceptable product of cut corallite; fully soaking the acceptable product of cut corallite in a phosphate solution, and performing a hydrothermal exchange reaction to obtain the coralline hydroxyapatite; wherein the cutting protective agent is a solution containing a polyol. The preparation method can significantly improve the cutting efficiency, broaden the cutting specifications and sizes, and significantly improve the yield of acceptable product, especially the yield of acceptable small-size products, which further broadens the application range of artificial bones.

15 Claims, 2 Drawing Sheets

(56)         References Cited

U.S. PATENT DOCUMENTS

| | | | |
|---|---|---|---|
| 7,547,449 B2 * | 6/2009 | Gower .................... | A61L 27/24 |
| | | | 435/177 |
| 2004/0091547 A1 | 5/2004 | Ben-Nissan et al. | |
| 2015/0182660 A1 | 7/2015 | Nazhat et al. | |
| 2020/0164104 A1 | 5/2020 | Sawadkar et al. | |
| 2020/0254142 A1 | 8/2020 | Jeong | |
| 2020/0316260 A1 | 10/2020 | Öhrlund et al. | |
| 2023/0405188 A1 | 12/2023 | Segal et al. | |

FOREIGN PATENT DOCUMENTS

| | | | |
|---|---|---|---|
| CN | 1055061 | A | 8/2000 |
| CN | 1069614 | A | 8/2001 |
| CN | 1404880 | A * | 3/2003 |
| CN | 1462638 | A | 12/2003 |
| CN | 1231269 | C | 12/2005 |
| CN | 1704129 | A | 12/2005 |
| CN | 1235645 | C | 1/2006 |
| CN | 100366301 | C | 2/2008 |
| CN | 100384488 | C | 4/2008 |
| CN | 101856514 | A | 10/2010 |
| CN | 103900885 | A | 7/2014 |
| CN | 104474591 | A | 4/2015 |
| CN | 113952504 | A | 1/2022 |
| CN | 116558919 | A | 8/2023 |
| EP | 3666298 | A1 | 6/2020 |
| WO | 2006096929 | A1 | 9/2006 |
| WO | 2019012295 | A1 | 1/2019 |
| WO | 2019/121688 | A1 | 6/2019 |

OTHER PUBLICATIONS

Machine translation of CN 103900885 A, Jul. 2, 2014. (Year: 2014).*

Machine translation of CN 1462638 A, Dec. 24, 2003. (Year: 2003).*

Chinese Search Report for CN Application No. 2025100457354, Coralline hydroxyapatite and preparation method and use thereof, issued on May 23, 2025.

Chinese Novelty Search Report, Coral hydroxyapatite, preparation method and application thereof, issued Apr. 1, 2025.

* cited by examiner

CORALLINE HYDROXYAPATITE AND PREPARATION METHOD THEREOF

CROSS-REFERENCE TO RELATED APPLICATION

This application claims priority under 35 U.S.C. § 119 or 365 to Chinese, application No. 202510045735.4, filed Jan. 10, 2025. The entire teachings of the above application is incorporated herein by reference.

TECHNICAL FIELD

The present disclosure belongs to the field of medical materials, and in particular relates to a coralline hydroxyapatite and a preparation method thereof.

BACKGROUND

Coralline hydroxyapatite artificial bone is a high-purity hydroxyapatite material prepared from natural coral as a raw material, which retains the original structural characteristics of coral and has a porous network structure with a pore size between 100 and 600 μm and a porosity of 30% to 70%. The physical structure, crystal arrangement and bone density of such a material under an electron microscope are very similar to those of human bones, so it has good biocompatibility and osteoconductivity. Coralline hydroxyapatite artificial bone has been used clinically and has shown good effects, so the coralline hydroxyapatite artificial bone products have broad application prospects.

The specifications of coralline hydroxyapatite artificial bone products are mostly bone powders (particles of different sizes), bone strips, bone blocks, bone slices and the like, while natural corals are mostly irregular and large in volume. Most specifications of coralline hydroxyapatite artificial bone products must be obtained by cutting and shaping. Therefore, the cutting of corallite is an essential and critical process for the production of coralline hydroxyapatite artificial bone products. In terms of physical properties, the corallite has a high hardness but is relatively fragile, making it difficult to cut. Especially when cut into small regular shapes, the corallite is more fragile, resulting in a low yield of acceptable corallite products.

At present, there are many patents about corallite, and especially the processing technology of corallite has been relatively mature. CN1055061C mainly involves a production method of using natural coral to carry out an anionic exchange reaction under hydrothermal conditions to convert it into a bioactive material hydroxyapatite. CN1203189A mainly involves soaking coral in high-concentration phosphate solution and carrying out a hydrothermal reaction under low and medium pressure conditions to prepare hydroxyapatite artificial bone. CN1069614C mainly introduces a chemical hole-enlarging technology for porous biological materials of natural coralline hydroxyapatite. CN1231269C mainly involves a method for preparing coralline hydroxyapatite artificial bone with an adjustable absorption speed. CN1235645C mainly involves the synthesis of an artificial bone by using natural coral as a raw material, and carrying out a hydrothermal replacement in diammonium phosphate plus hydrothermal liquid system under a high-temperature and high-pressure condition. CN100366301C involves soaking coralline hydroxyapatite in phosphoric acid, phosphate or a mixed solution thereof for a certain period of time at a certain temperature, and then heating it for conversion reaction to produce a coralline hydroxyapatite artificial bone with β-tricalcium phosphate on the surface thereof. CN100384488C involves after washing natural coral with water, rinsing and drying, etching its pores with dilute hydrochloric acid, and soaking and reacting in a saturated phosphate solution to prepare an absorbable hydroxyapatite artificial bone. The existing technology focuses on the production method of coralline hydroxyapatite artificial bones, which changes different processing ways, but does not mention how to process natural corallite into the required specifications of artificial bone. The cutting process of corallite is an essential step in corallite processing, and the brittleness of corallite determines that the corallite is prone to breakage during cutting, but there is no research or report about it.

Currently, when corallite is cut, the cutting efficiency is relatively low; on the other hand, when corallite is cut, the limit of cutting size is relatively large; thirdly, when coralline hydroxyapatite is prepared into product specifications with certain shapes such as blocks and strips, it is prone to fracture during cutting, and the yield of the acceptable product is relatively low.

Therefore, it is necessary and meaningful to find a cutting protective agent corallite and perform a pretreatment process on the corallite to improve the yield of acceptable product of coralline hydroxyapatite.

SUMMARY

In order to solve the above technical problem, an object of the present disclosure is to provide a coralline hydroxyapatite and a preparation method thereof.

In order to achieve the above object, the present disclosure provides a coralline hydroxyapatite having a pore size of 30 μm to 1300 μm, a porosity of 50% to 70%, and a conversion rate of 50% or more.

According to a specific embodiment of the present disclosure, the coralline hydroxyapatite has a conversion rate of 70% or more.

According to a specific embodiment of the present disclosure, the coralline hydroxyapatite has a conversion rate of 90% or more.

The pore structure of the coralline hydroxyapatite of the present disclosure is similar to that of human cancellous bone, and the pores are interconnected.

The pore size of 30 μm to 1300 μm in the present disclosure refers to the range of pore size distribution.

The coralline raw material of the coralline hydroxyapatite product of the present disclosure may be natural corallite. Preferably, the natural corallite includes *Porites* corallite and *Goniopora* corallite.

For the coralline hydroxyapatite prepared from *Porites* corallite as a raw material, the range of pore size distribution is generally 30 μm to 800 μm; for the coralline hydroxyapatite prepared from *Goniopora* corallite as a raw material, the range of pore size distribution is generally 90 μm to 1300 μm.

The present disclosure further provides a method for preparing the coralline hydroxyapatite mentioned above, comprising:

soaking pretreated corallite in a cutting protective agent, and then cutting to obtain cut corallite, and screening for cut corallite that meets a cutting size requirement to obtain an acceptable product of cut corallite;

fully soaking the acceptable product of cut corallite in a phosphate solution, and performing a hydrothermal exchange reaction to obtain the coralline hydroxyapatite;

wherein the cutting protective agent is a solution containing a polyol.

In the above method, the mass fraction of the polyol is >20%, preferably 30 to 80%, more preferably 30% to 50%, based on the total mass of the cutting protective agent;

In the above method, preferably, the polyol is selected from one or a combination of two or more of glycerol, ethylene glycol, sorbitol, and butanediol.

In the above method, the soaking in the cutting protective agent is carried out for 3 to 24 hours.

In the above method, the corallite is pretreated by steps including:

removing dust from natural corallite, soaking in a sodium hypochlorite solution or a hydrogen peroxide solution, washing, and drying for later use.

In the above method, the phosphate solution has a concentration of 1 to 5 mol/L.

In the above method, the hydrothermal exchange reaction is carried out at a pressure of 1 to 3 MPa and a temperature of 120 to 240° C. for 5 to 48 h.

In the above method, the cutting is performed with a bandsaw.

In the above method, preferably, the cutting is performed at a cutting speed of 1.6 to 3 cm/s, more preferably 1.9 to 2.4 cm/s.

In the above method, the limit value of the cutting size is 0.1 to 0.5 cm, preferably 0.3 to 0.5 cm.

During cutting of corallite, the smaller the cutting size, the more fragile it is. However, when it is treated with the polyol-based cutting protective agent of the present disclosure, the minimum value of the cutting specification and size can be reduced, the yield of cutting acceptable small-size products can be improved, and the integrity of the cut products can be guaranteed.

The cutting method of the present disclosure can be used to obtain coralline hydroxyapatite products of the following sizes: (0.1-1) cm×(0.1-1) cm×(0.1-1) cm, (1-10) cm×(1-10) cm×(1-10) cm, (5-20) cm×(5-20) cm×(5-20) cm; for example, the following sizes can be obtained: 0.1 cm×0.1 cm×0.1 cm, 0.2 cm×0.2 cm×0.2 cm, 0.1 cm×0.2 cm×0.2 cm, 0.1 cm×0.3 cm×0.3 cm, 0.1 cm×0.3 cm×0.5 cm, 0.3 cm×0.3 cm×0.5 cm, 0.4 cm×0.4 cm×0.4 cm, 0.4 cm×0.4 cm×0.5 cm, 0.3 cm×0.4 cm×0.5 cm, 0.5 cm×0.5 cm×0.5 cm, 0.6 cm×0.6 cm×0.6 cm, 0.7 cm×0.7 cm×0.7 cm, 0.8 cm×0.8 cm×0.8 cm, 0.9 cm×0.9 cm×0.9 cm, 1.0 cm×1.0 cm×1.0 cm, 1.0 cm×1.0 cm×5.0 cm, 2.0 cm×2.0 cm×2.0 cm, 5.0 cm×5.0 cm×5.0 cm, 10.0 cm×10.0 cm×10.0 cm.

The coralline hydroxyapatite product of the present disclosure may be further cut and/or polished.

In the above method, the yield of the acceptable product of cut corallite is 30 to 70%, when the cutting size is ≤0.3 cm.

In the above method, the yield of the acceptable product of cut corallite is 30 to 99%, when the cutting size is >0.3 cm.

The present disclosure also provides a coralline hydroxyapatite obtained by the above method.

The present disclosure also provides a method for treating bone defects or for bone repair, comprising implanting or filling the above coral hydroxyapatite into the site of the bone defect or bone repair.

The coral hydroxyapatite is consistent with the inorganic components of natural bone and has good biocompatibility. At the same time, the high porosity and microporous structure of the coral hydroxyapatite can provide scaffold structure for bone cells, guide the growth of new bone tissue along its surface, and promote the repair of bone defects. For example, after tooth extraction, the coral hydroxyapatite material is filled into the extraction socket for site preservation, which is the increment of dental implant bone; Or in bone trauma repair, the coral hydroxyapatite material is placed into long bone defects such as tibia and femur to fill, so as to promote bone defect repair; Alternatively, during spinal fusion, the interbody bone defect is reconstructed by filling the interbody bone defect with the coral hydroxyapatite material.

According to a specific embodiment of the present disclosure, the method for preparing the coralline hydroxyapatite comprises:

(1) ultrasonically washing natural corallite to remove impurity, dust and the like on the surface, then soaking it in a sodium hypochlorite solution or a hydrogen peroxide solution, followed by washing with purified water and drying for later use;

(2) soaking the corallite in a solution containing a polyol with hydroxyl groups and a concentration of no less than 20% to fully soak the corallite for 3-24 hours;

(3) cutting and polishing the corallite processed in step (2) to prepare it into various shapes and specifications as required, and then washing and drying it;

(4) placing the corallite processed in step (3) in a reactor, adding a phosphate solution of 1-5 mol/L to fully soak the corallite, and performing a hydrothermal reaction at a pressure of 1-3 MPa and 120-240° C. for 5-48 hours to obtain the coralline hydroxyapatite;

(5) washing and drying the coralline hydroxyapatite obtained in step (4), and then packaging and irradiating for sterilization.

The present disclosure uses a polyol to soak the corallite, so that the corallite is fully soaked to increase the lubricity of the corallite, and in the subsequent cutting and polishing process, the corallite is easier to cut and shape, the cutting efficiency of corallite is improved, the specification and size of the corallite artificial bone are broadened, and the yield of acceptable corallite artificial bone products is also improved, which can better meet the requirements of bone repair.

DETAILED DESCRIPTION

Figure 1:
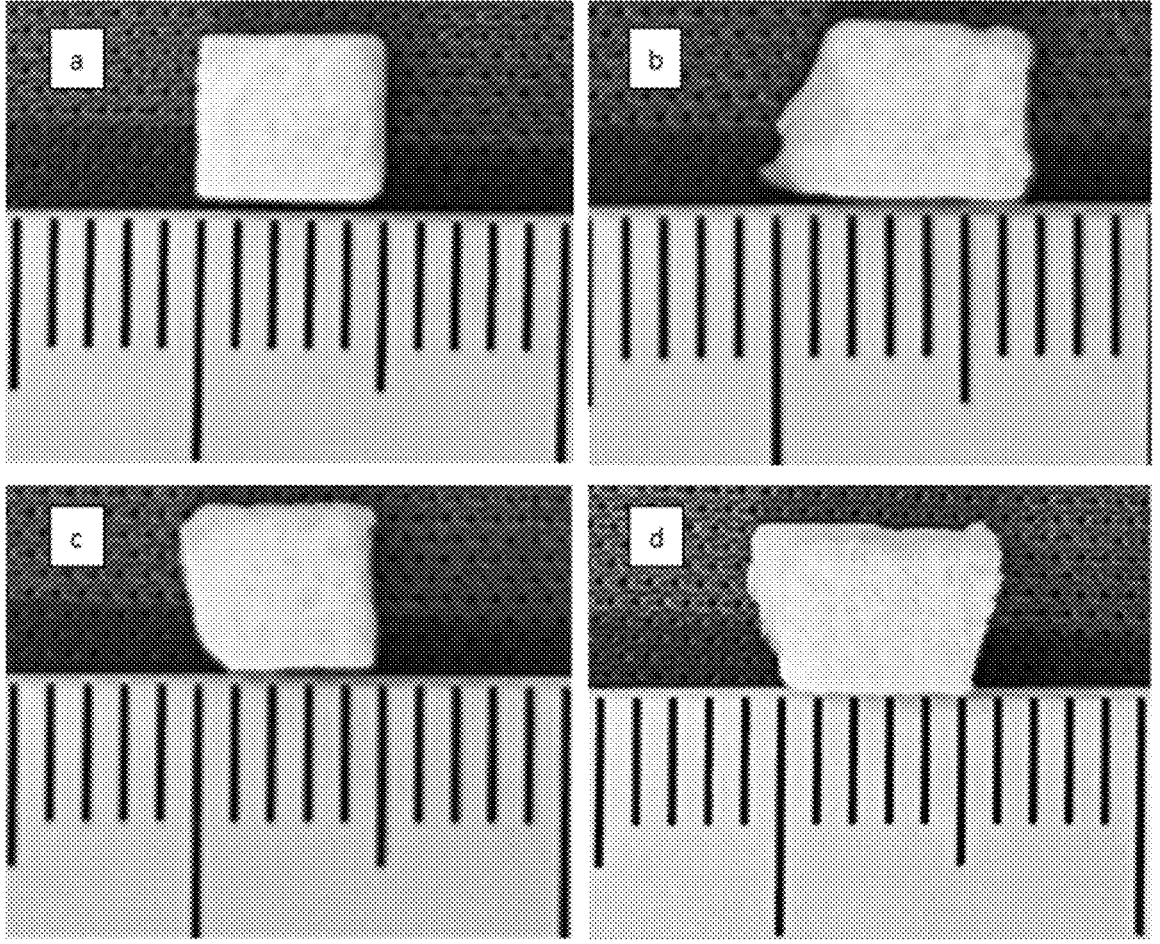
FIG. 1 is an appearance diagram of the corallite after cutting, where a is the cut corallite in Example 1, b is the cut corallite in Comparative Example 1, c is the cut corallite in Comparative Example 3, and d is the cut corallite in Comparative Example 4.

In order to have a clearer understanding of the technical features, purposes and beneficial effects of the present disclosure, the technical solutions of the present disclosure will now be described below in details, but it should not be construed as limiting the implementable scope of the present disclosure.

In actual production, those skilled in the art will understand that some relevant process steps may be adjusted or increased or decreased, provided that qualified products can be obtained.

Example 1

*Porites* is taken as an example. Natural *Porites* corallite was ultrasonically washed to remove impurity, powder and the like on the surface, subsequently soaked in 30% hydrogen peroxide solution, and then washed with purified water and dried.

Glycerin was mixed with water to prepare a 40% (wt) glycerin solution. The corallite was soaked in the 40% (wt) glycerin solution to fully soak the corallite for 10 hours. Then it was cut with a bandsaw (equipment model: JBS-260, saw blade specification: 1710*9.5*0.35 mm*14 TPI). The cutting efficiency and cutting limit were compared, and the yield of the acceptable product of cut samples under the corresponding specifications was statistically analyzed. The results are shown in Table 1. The cut representative samples of 0.5×0.5×0.5 cm³ specification are shown in a of FIG. 1. The corallite samples of specified sizes were placed in a reactor, and a diammonium phosphate solution of 3 mol/L was added and reacted at 180° C. for 24 hours, followed by washing, drying, packaging, and sterilizing to obtain coralline hydroxyapatite. The pore size thereof is shown in Table 1, and the scanning electron microscope image is shown in FIG. 2. The range of pore size distribution is 30 μm to 800 μm. The conversion rate of the coralline hydroxyapatite product prepared in this example is tested to be about 61.7%.

Example 2

*Goniopora* is a large-pore coral that is more fragile when cut. *Goniopora* is taken as an example. Natural *Goniopora* corallite was ultrasonically washed to remove impurity, powder and the like on the surface, subsequently soaked in 30% hydrogen peroxide solution, and then washed with purified water and dried.

The corallite was soaked in a 30% (wt) glycerin solution to fully soak the corallite for 4 hours. Then it was cut with a bandsaw (equipment model: JBS-260, saw blade specification: 1710*9.5*0.35 mm*14 TPI). The cutting efficiency and cutting limit were compared, and the yield of the acceptable product of cut samples under the corresponding specifications was statistically analyzed. The results are shown in Table 1. The corallite samples of specified sizes were placed in a reactor, and a diammonium phosphate solution of 3 mol/L was added and reacted at 180° C. for 24 hours, followed by washing, drying, packaging, and sterilizing to obtain coralline hydroxyapatite. The pore size thereof is shown in Table 1, and the range of pore size distribution is 90 μm to 1300 μm. The conversion rate is tested to be about 66.3%.

Comparative Example 1

*Porites* is taken as an example. Natural *Porites* corallite was ultrasonically washed to remove impurity, powder and the like on the surface, subsequently soaked in 30% hydrogen peroxide solution, and then washed with purified water and dried.

The corallite was cut with a bandsaw (equipment model: JBS-260, saw blade specification: 1710*9.5*0.35 mm*14 TPI). The cutting efficiency and cutting limit were compared, and the yield of the acceptable product of cut samples under the corresponding specifications was statistically analyzed. The results are shown in Table 1. The cut representative samples of 0.5×0.5×0.5 cm³ specification are shown in b of FIG. 1. The corallite samples of specified sizes were placed in a reactor, and a diammonium phosphate solution of 3 mol/L was added and reacted at 180° C. for 24 hours, followed by washing, drying, packaging, and sterilizing to obtain coralline hydroxyapatite. The pore size thereof is shown in Table 1.

Comparative Example 2

*Goniopora* is a large-pore coral that is more fragile when cut. *Goniopora* is taken as an example. Natural *Goniopora* corallite was ultrasonically washed to remove impurity, powder and the like on the surface, subsequently soaked in 30% hydrogen peroxide solution, and then washed with purified water and dried.

The corallite was cut with a bandsaw (equipment model: JBS-260, saw blade specification: 1710*9.5*0.35 mm*14 TPI). The cutting efficiency and cutting limit were compared, and the yield of the acceptable product of cut samples under the corresponding specifications was statistically analyzed. The results are shown in Table 1. The corallite samples of specified sizes were placed in a reactor, and a diammonium phosphate solution of 3 mol/L was added and reacted at 180° C. for 24 hours, followed by washing, drying, packaging, and sterilizing to obtain coralline hydroxyapatite. The pore size thereof is shown in Table 1.

Comparative Example 3

*Porites* is taken as an example. Natural *Porites* corallite was ultrasonically washed to remove impurity, powder and the like on the surface, subsequently soaked in 30% hydrogen peroxide solution, and then washed with purified water and dried.

The corallite was soaked in a 5% (wt) glycerin solution to fully soak the corallite for 15 hours. Then it was cut with a bandsaw (equipment model: JBS-260, saw blade specification: 1710*9.5*0.35 mm*14 TPI). The cutting efficiency and cutting limit were compared, and the yield of the acceptable product of cut samples under the corresponding specifications was statistically analyzed. The results are shown in Table 1. The cut representative samples of 0.5×0.5×0.5 cm³ specification are shown in c of FIG. 1. The corallite samples of specified sizes were placed in a reactor, and a diammonium phosphate solution of 3 mol/L was added and reacted at 180° C. for 24 hours, followed by washing, drying, packaging, and sterilizing to obtain coralline hydroxyapatite. The pore size thereof is shown in Table 1.

Comparative Example 4

*Porites* is taken as an example. Natural *Porites* corallite was ultrasonically washed to remove impurity, powder and the like on the surface, subsequently soaked in 30% hydrogen peroxide solution, and then washed with purified water and dried.

Carboxymethyl cellulose (polysaccharide) was dissolved in water to prepare a 0.06% (wt) carboxymethyl cellulose solution. The corallite was soaked in a 0.06% (wt) carboxymethyl cellulose solution to fully soak the corallite for 24 hours. Then it was cut with a bandsaw (equipment model: JBS-260, saw blade specification: 1710*9.5*0.35 mm*14 TPI). The cutting efficiency and cutting limit were compared, and the yield of the acceptable product of cut samples under the corresponding specifications was statistically analyzed. The results are shown in Table 1. The cut representative samples of 0.5×0.5×0.5 cm³ specification are shown in d of FIG. 1. The corallite samples of specified sizes were placed in a reactor, and a diammonium phosphate solution of 3 mol/L was added and reacted at 180° C. for 24 hours, followed by washing, drying, packaging, and sterilizing to obtain coralline hydroxyapatite. The pore size thereof is shown in Table 1.

TABLE 1

Statistic cutting results of different corallites after different treatments

| Classifi-cation | Cutting efficiency (cm/s) | Cutting limit (cm) | Yield of acceptable product | | | | Pore size (µm) |
| | | | $0.3 \times 0.3 \times 0.5$ cm$^3$ | $0.5 \times 0.5 \times 0.5$ cm$^3$ | $1.0 \times 1.0 \times 1.0$ cm$^3$ | $1.0 \times 1.0 \times 5.0$ cm$^3$ | |
| --- | --- | --- | --- | --- | --- | --- | --- |
| Example 1 | 2.4 | 0.3 | 69.2% | 82.8% | 89.7% | 90.6% | 30 to 800 |
| Example 2 | 1.9 | 0.5 | 30.2% | 72.1% | 86.7% | 90.7% | 90 to 1300 |
| Comparative Example 1 | 1.2 | 0.5 | 15.8% | 53.8% | 59.3% | 77.3% | 30 to 800 |
| Comparative Example 2 | 0.8 | 1.0 | 5.6% | 31.6% | 56.7% | 61.1% | 90 to 1300 |
| Comparative Example 3 | 1.5 | 0.5 | 22.4% | 63.3% | 67.6% | 81.3% | 30 to 800 |
| Comparative Example 4 | 1.3 | 0.5 | 19.4% | 54.5% | 61.3% | 77.4% | 30 to 800 |

Note: Acceptable product refers to the cut corallite sample whose specification and dimension are consistent with the predetermined requirements with an error of no greater than +1 mm. The yield of acceptable product=the number of acceptable product of cut corallite/the total number of cut corallite samples×100%. The subsequent processing after cutting has little effect on the size and appearance of the corallite sample, so the yield of acceptable product herein represents the yield of acceptable product of coralline hydroxyapatite (artificial bone).

Figure 2:
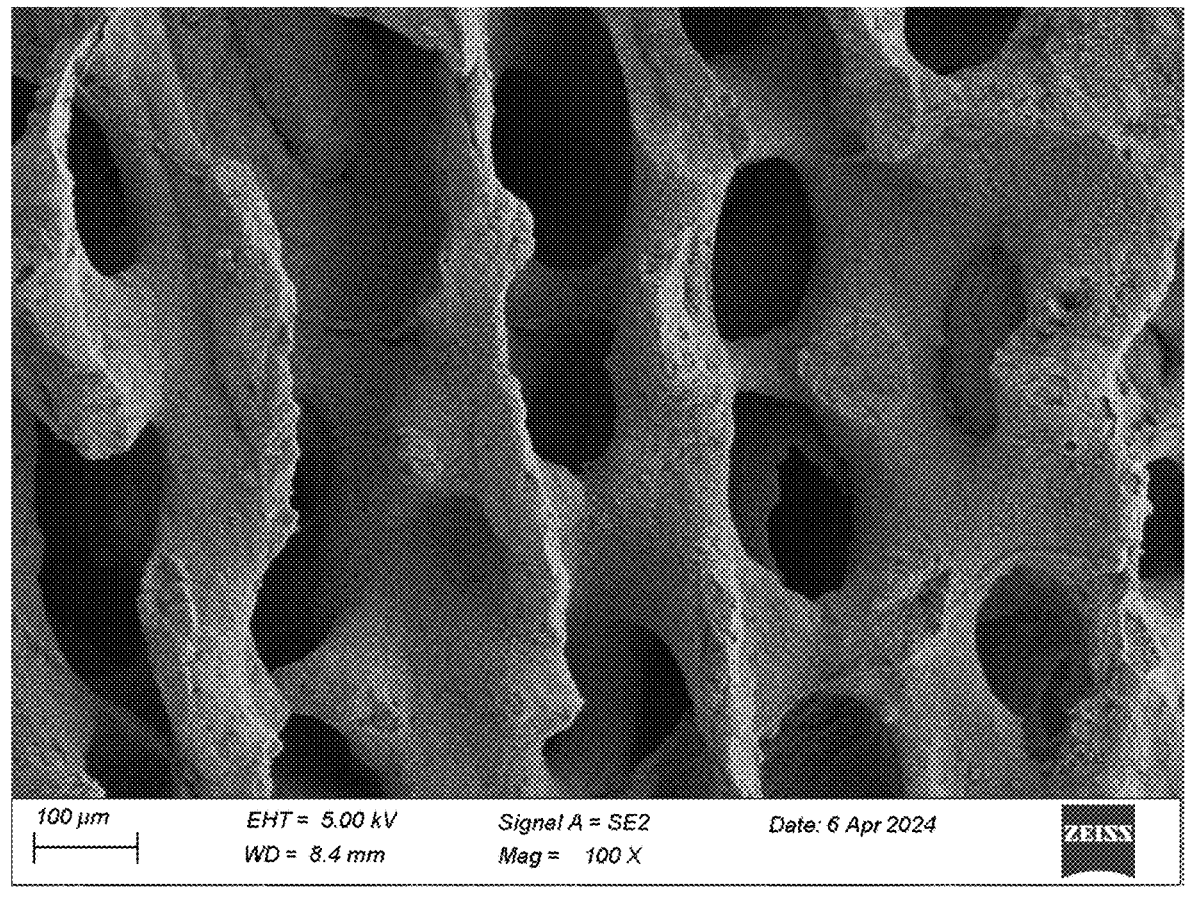
FIG. 2 is a scanning electron microscope image (100×) of the coralline hydroxyapatite product in Example 1.

By comparison, it can be seen that when the cutting protective agent is not added or a polysaccharide-based substance (non-polyol protective agent) is added to corallite or the concentration of protective agent is too low, it is easy to break and fracture during cutting, and the cutting surface is uneven, as shown in b to d of FIG. 1; the cutting speed does not exceed 1.5 cm/s (this cutting speed is based on the limit of cutting size, and an acceptable product would hardly be obtained if it is exceeded), and the cutting limit value is 0.5 to 1.0 cm; however, when the cutting protective agent is added and the pretreatment is done, the corallite is less likely to fracture during cutting, the cutting speed is 1.9 to 2.4 cm/s, the cutting limit value is 0.3 to 0.5 cm, and a good cutting morphology can be formed, as shown in a of FIG. 1.

In the different treatment groups of corallites, for the yield of acceptable product under the same specification, as the product size increases, the yield of acceptable product will also increase. When a certain concentration of polyol cutting protective agent is added and the pretreatment is done, the yield of acceptable product will be significantly improved as compared with the case without adding protective agent. Especially when cutting small-size products, the addition of a certain concentration of polyol cutting protective agent and the presence of pretreatment has great advantages. After the corallite is cut, it undergoes multiple washing processes. The polyol is easily soluble in water, so the final coralline hydroxyapatite product is tested to have no protective agent residue. The conversion rate of the coralline hydroxyapatite of required specifications and sizes obtained by the method of the present disclosure is 50% or more, so as to be suitable for its application performance as artificial bone and achieve the required degradation speed.

In summary, by adding a certain concentration of specific cutting protective agent and performing pretreatment, the cutting efficiency can be significantly improved, the cutting specifications can be broadened, and the yield of acceptable product, especially the yield of acceptable small-size products can be significantly improved. Therefore, the present disclosure has a great significance for the treatment of corallite and further broadens the application range of artificial bones.

What is claimed is:

1. A method for preparing a coralline hydroxyapatite, comprising:
   soaking pretreated corallite in a cutting protective agent, and then cutting it to obtain cut corallite, and screening for cut corallite that meets a cutting size requirement to obtain an acceptable product of cut corallite;
   fully soaking the acceptable product of cut corallite in a phosphate solution, and performing a hydrothermal exchange reaction to obtain the coralline hydroxyapatite;
   wherein the cutting protective agent is a solution containing a polyol.

2. The method according to claim 1, wherein the mass fraction of the polyol is ≥20% based on a total mass of the cutting protective agent.

3. The method according to claim 1, wherein, the polyol is selected from one or a combination of two or more of glycerol, ethylene glycol, sorbitol, and butanediol.

4. The method according to claim 1, wherein, the soaking in the cutting protective agent is carried out for 3 to 24 hours.

5. The method according to claim 1, wherein the corallite is pretreated by steps including:
   removing dust from the corallite, soaking the corallite in a sodium hypochlorite solution or a hydrogen peroxide solution, washing, and drying for later use.

6. The method according to claim 1, wherein the phosphate solution has a concentration of 1 to 5 mol/L.

7. The method according to claim 1, wherein, the hydro-thermal exchange reaction is carried out at a pressure of 1 to 3 MPa and a temperature of 120 to 240° C. for 5 to 48 h.

8. The method according to claim 1, wherein the cutting is performed with a bandsaw.

9. The method according to claim 8, wherein, the cutting is performed at a cutting speed of 1.6 to 3 cm/s.

10. The method according to claim 9, wherein, the cutting is performed at a cutting speed of 1.9 to 2.4 cm/s.

11. The method according to claim 1, wherein the limit value of the cutting size is 0.1 to 0.5 cm.

12. The method according to claim 11, wherein the limit value of the cutting size is 0.3 to 0.5 cm.

13. The method according to claim 1, wherein the yield of the acceptable product of cut corallite is 30% to 70%, when the cutting size is ≤0.3 cm.

14. The method according to claim 1, wherein the yield of the acceptable product of cut corallite is 30% to 99%, when the cutting size is >0.3 cm.

15. The method of claim 1, wherein the coralline hydroxy-apatite has a pore size of 30 μm to 1300 μm, a porosity of 50% to 70%, and a conversion rate of 50% or more.

* * * * *